(12) United States Patent
Raab et al.

(10) Patent No.: US 9,993,598 B2
(45) Date of Patent: Jun. 12, 2018

(54) DISPLAY ARRANGEMENT FOR A DRUG DELIVERY DEVICE

(71) Applicant: SANOFI-AVENTIS DEUTSCHLAND GMBH, Frankfurt am Main (DE)

(72) Inventors: Steffen Raab, Frankfurt am Main (DE); Ivana Berger, Frankfurt am Main (DE); Sandra Brose, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1067 days.

(21) Appl. No.: 14/347,560

(22) PCT Filed: Oct. 4, 2012

(86) PCT No.: PCT/EP2012/069606
§ 371 (c)(1),
(2) Date: Mar. 26, 2014

(87) PCT Pub. No.: WO2013/050461
PCT Pub. Date: Apr. 11, 2013

(65) Prior Publication Data
US 2014/0236092 A1    Aug. 21, 2014

(30) Foreign Application Priority Data
Oct. 6, 2011    (EP) .................................. 11184118

(51) Int. Cl.
*A61M 5/00*    (2006.01)
*A61M 3/00*    (2006.01)
(Continued)

(52) U.S. Cl.
CPC ......... *A61M 5/31525* (2013.01); *G02B 26/02* (2013.01); *G09B 23/28* (2013.01); *A61M 2005/3126* (2013.01)

(58) Field of Classification Search
CPC ...... A61M 2005/3126; A61M 5/31525; G02B 26/02; G09B 23/28
(Continued)

(56) References Cited

U.S. PATENT DOCUMENTS 533,575 A    2/1895 Wilkens
3,248,050 A * 4/1966 Dickson ................... G06C 3/00
235/89 R
(Continued)

FOREIGN PATENT DOCUMENTS

DE    10106367 A1    8/2002
EP    0937471 A2    8/1999
(Continued)

OTHER PUBLICATIONS

Office Action issued in Japanese Patent Application No. 2014-533889 dated Feb. 29, 2017.
(Continued)

*Primary Examiner* — Jason Flick
(74) *Attorney, Agent, or Firm* — McCarter & English, LLP (57) ABSTRACT

The present invention relates to a display arrangement for a drug delivery device, comprising: a first display member comprising numerous surface portions having at least two different but interrelated appearances and being alternately arranged along a first direction, and a second display member comprising a light modulating structure to modulate visible light emanating from the first display member, wherein first and second display members are movably disposed relative to each other along the first direction to simultaneously reveal and/or to conceal at least two surface portions of interrelated appearance.

18 Claims, 4 Drawing Sheets

(51) Int. Cl.
*G02B 26/02* (2006.01)
*G02B 26/00* (2006.01)
*A61M 5/315* (2006.01)
*G09B 23/28* (2006.01)
*A61M 5/31* (2006.01)

(58) Field of Classification Search
USPC ........................................................ 604/111
See application file for complete search history.

(56) References Cited

U.S. PATENT DOCUMENTS

| | | | |
|---|---|---|---|
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A * | 5/1997 | Petersen ............ | A61M 5/31551 222/309 |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 7,407,492 B2 | 8/2008 | Gurtner | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2009/0275916 A1 | 11/2009 | Harms et al. | |
| 2010/0274198 A1 | 10/2010 | Bechtold | |

FOREIGN PATENT DOCUMENTS

| | | |
|---|---|---|
| EP | 0937476 A2 | 8/1999 |
| JP | 2000-288236 A | 10/2000 |
| JP | 2005055530 A | 3/2005 |
| JP | 2007-508573 A | 4/2007 |
| WO | 9938554 A1 | 8/1999 |
| WO | 0110484 A1 | 2/2001 |
| WO | 2005/031687 A2 | 4/2005 |
| WO | 2010020311 A1 | 2/2010 |

OTHER PUBLICATIONS

English Translation of Abstract of Japanese Patent Application No. 2005-055530 dated May 24, 2017.

* cited by examiner

Fig. 6

DISPLAY ARRANGEMENT FOR A DRUG DELIVERY DEVICE

CROSS REFERENCE TO RELATED APPLICATIONS

The present application is a U.S. National Phase Application pursuant to 35 U.S.C. § 371 of International Application No. PCT/EP2012/069606 filed Oct. 4, 2012, which claims priority to European Patent Application No. 11184118.5 filed Oct. 6, 2011. The entire disclosure contents of these applications are herewith incorporated by reference into the present application.

FIELD OF INVENTION

The present invention relates to a display arrangement for a drug delivery device, and in particular to a display element to illustrate conditions of use or various states of a pen-type injector.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially designed and intended for home medication therefore need to be robust in construction and should be easy to use. Furthermore, manipulation and general handling of the device and its components should be intelligible and easy understandable. In particular setting and dispensing of a dose of the medicament should be easy to conduct and has to be safe and reliable.

Typically, such drug delivery devices comprise a housing adapted to receive a cartridge at least partially filled with the medicament to be dispensed. The device further comprises a drive mechanism, typically having a displaceable piston rod which is adapted to operably engage with a piston of the cartridge. By means of the drive mechanism and its piston rod, the piston of the cartridge can be displaced in a distal or dispensing direction and may therefore expel a predefined amount of the medicament via a piercing assembly which is to be releasably coupled with a distal end section of the housing of the drug delivery device, e.g. with a cartridge holder.

In particular with users or patients being physically or visually impaired correct handling of the device is sometimes cumbersome. Moreover, especially prior or after replacement of an empty cartridge, the patient has to be informed, that an initial or final dose is to be set and dispensed or that an initiating priming procedure has to be conducted. Moreover, the device may provide visual or readable indicators or display elements in order to inform the user or patient of the actual status and configuration of the device. Such information should be clearly and unambiguously legible, even for visually impaired persons.

Document DE 101 06 367 A1 for instance discloses a pen-type injector comprising a magnifying optic to support reading of a dose scale.

Moreover, document WO 2010/020311 A1 discloses a first and a second lens arrangement mutually acting together to increase the legibility of a set dosage value, preferably to counteract false readings of a selected dosage setting.

Such optical aids may enhance secure and safe handling as well as operation of drug delivery devices. However, visual illustration of different device states always requires a comparatively large mutual displacement of optical aids and display members carrying the information to be displayed and/or magnified. Typically, spatial relative displacement of the various components is at least in the range of the size of the information to be displayed.

It is therefore an object of the present invention to provide an improved display arrangement adapted to display different configurations or device states on the basis of a minimum displacement of a display member and an optical aid. Moreover, the display arrangement according to the present invention should be robust, reliable as well as cost efficient in terms of manufacturing and assembly. Also, the display arrangement should be easily legible and should visually provide different information with a large contrast.

SUMMARY

The present invention relates to a display arrangement for a drug delivery device. The display arrangement comprises a first display member having numerous surface portions that are preferably regularly arranged on the surface of the first display member. The various surface portions comprise at least two different but interrelated appearances and are further alternately arranged along a first direction on the visible surface of the first display member. The display arrangement further has a second display member comprising a light modulating structure to modulate visible light emanating from the first display member.

First and second display members are moveably disposed relative to each other along the first direction to simultaneously reveal and/or to simultaneously conceal at least two surface portions of interrelated appearance. In particular, the first display member comprises information or is imprinted with information to be displayed to a user while the second display member substantially acts as an optical aid.

In particular, the first display member comprises at least two different information carriers which reflect in interrelated surface portions. For instance, the first display member comprises two or more symbols that are imprinted on the first display member in a fragmented but regular, e.g. in a mutually staggered order. The light modulating structure of the second display member matches with the fragmented information and depending on a mutual position or movement of first and second display members, those fragments or surface portions that relate to a first symbol complement each other to reveal the first symbol while concealing the second symbol. Similarly, by displacing first and second display members relative to each other those surface portions that relate to the second symbol may be revealed at the expense of the visibility of the first symbol.

In particular, the first display member comprises spatially distributed surface portions at least a part of which being mutually interrelated and complement each other to illustrate a predefined, e.g. a first information. Other surface portions of the first display member may be arranged in a different way and may also interrelate to each other but serve to compose and/or to complement a different, e.g. second information. Alternate and selective revealing and/or concealing of interrelated surface portions, each of which referring to a particular information, only requires to displace or to move first and second display members relative to each other by a distance which is governed by the size of a single surface portion.

The total size of the information provided by the display arrangement may be multiple times larger compared to the size of a surface portion. Hence, already a rather small and minimal relative movement of first and second display members may effectuate to change the overall appearance of the entire display arrangement and/or of its first and/or second display members.

This way, a relative movement in the range of 1 to 2 mm or less may suffice to totally change the outer appearance of the entire display arrangement featuring a size in the range of several millimeters or even centimeters. This way, a minimal displacement of first and second display members can provide a rather large, clearly visible and contrast enhanced display modification.

According to a first embodiment, first and second display members are arranged at a distance from each other in a substantially overlapping configuration. Preferably, the surfaces of first and second display members are substantially equal. First and second display members may be of flat or even-shaped geometry. Alternatively, first and second display members may comprise an arc-shaped or cylindrical geometry. First and second display members are preferably arranged in a kind of overlapping configuration, such that their respective surface normals extend substantially parallel with respect to each other.

The distance between first and second display members may vary according to the design and geometry of the arrangement of surface portions of interrelated appearances of the first display member. The distance may further depend or may be correlated with the optical light modulating properties of the second display member.

According to a further aspect, the first and second display members are designed and/or are mutually arrangeable with respect to each other to selectively reveal and/or to selectively conceal all surface portions of the first display member that are interrelated to each other. This way, depending on the mutual position or orientation of first and second display members, preferably all surface portions belonging to a first information are revealed while those surface portions that relate to a different, second information are concealed. By displacing first and second display members relative to each other, an opposite configuration, in which the first information is concealed and the second information is revealed can be attained.

First and second display members may be slidably displaceable and/or rotatably displaceable with respect to each other depending on the overall geometry of the display arrangement and its display members.

According to a further embodiment, at least a portion of the first display member is substantially reflective or transmissive for light in the visible spectrum. In case the first display member is reflective, the entire display arrangement is designed to be operated in reflection geometry. In case the first display member is substantially or at least partially transmissive for light in the visible spectrum, the display arrangement may be also driven in transmission geometry. Moreover, the first display member may comprise selected surface portions being transmissive while other surface portions are substantially reflective. Transmissive display members and/or surface portions are of particular benefit in embodiments, where the drug delivery device and/or the display arrangement comprises an internal light source, e.g. to indicate a particular status or configuration of the drug delivery device.

When the first display member and/or its surface portions are substantially non-transparent and are therefore intended to be operated in reflection geometry only, the second display member is accordingly designed to allow bidirectional transmission of light in the visible spectrum. In such a configuration, a light source, e.g. ambient light, is provided externally, such that light for reading of the information provided on the first display element propagates through the second display member to become reflected on the surface of the first display member prior to become modulated by the second display member. This way, the second display member may serve to modulate an incident illumination as well as light being reflected from the first display member disposed underneath the second display member.

According to a further preferred embodiment, the surface portions of the first display member that are interrelated to each other are periodically arranged along the first direction. Also, depending on the number of different information to be displayed by the display arrangement, the first display member is divided into respective groups of surface portions or sections, wherein neighbouring or adjacently located surface portions are interrelated or assigned to the respective information in a periodic and/or alternating way. Preferably, surface portions are of substantially equal size, at least along the first direction. This way, equidistant displacement of first and second display members may entirely reveal or conceal respective information.

For instance, if the first display member is designed to provide three different information, e.g. in form of different colors or different symbols, first, second and third surface portions, each of which being interrelated to first, second and third information, respectively, are arranged in a repeating and periodic way along the first direction, e.g.: first, second, third; first, second, third; first, . . . .

In a further embodiment, the light modulating structure corresponds with the size and/or with the distance between interrelated surface portions of the first display member. In particular, mutual arrangement, in particular mutual distance and orientation of first and second display members as well as the individual design of first and second display members is chosen such, that the light modulating structure of the second display member is enabled to substantially reveal and/or to substantially conceal all surface portions of the first display member that are interrelated with each other in order to visually illustrate a particular information.

For this purpose and according to another preferred embodiment, a periodicity of the surface portions of the first display member matches with a periodicity of the light modulating structure of the second display member. The light modulating structures of the second display member may be substantially equal in size compared to the size of the surface portions of the first display member. However, depending on the optical path between first and second display members, geometric size or periodic structures of first and second display member may also vary.

According to a further embodiment, the light modulating structure of the second display member comprises at least two apertures arranged along the first direction according to a predefined distance-scheme. The apertures typically match in geometry and size with the geometry and arrangement of the surface portions of the first display member. In particular, the apertures of the light modulating structure are separated by light absorbing cover portions.

In a further preferred aspect, the light modulating structure of the second display member comprises at least two light diffracting and/or light reflecting portions arranged along the first direction. In particular, the light modulating arrangement may comprise a refractive or diffractive optical component, by way of which light emanating from the first display member can be spatially modulated to selectively conceal and/or reveal selected surface portions of the first display member. The light modulating arrangement may comprise amplitude- and/or phase-modulating means and may further provide either a static or dynamic and reconfigurable light modulating arrangement.

Preferably, the light modulating arrangement is of static type and therefore requires mutual displacement relative to the first and/or second display member in order to selectively reveal and/or conceal selected information provided on the first display member.

In a preferred embodiment the light modulating arrangement comprises at least two magnifying lens portions adjacently arranged along the first direction. Hence, the light modulating structure may comprise a lens-like component featuring a rippled or undulated surface preferably facing away from the first display member. The magnifying lens portions are typically of convex or plane-convex shape and provide magnification of the surface portion of the first display member positioned underneath.

In a further preferred embodiment, the surface portions of the first display member are interrelated to each other by their color, by a symbol, by a number and/or by a letter or by any other kind of visually displayable information. In particular, the first display member may comprise numerous stripes of red of green color periodically and alternately arranged along the first direction. Depending on a mutual position and/or orientation of first and second display members, the entire display arrangement may then appear entirely red or entirely green.

In still another embodiment, the first and/or the second display member is integrated into a housing component of the drug delivery device. Preferably, the second display member may be imprinted on the outer circumference of the drug delivery device and/or of a housing component thereof. Then, the second display member may be displaceably arranged along the first direction on the housing component to selectively reveal and/or to selectively conceal interrelated surface portions of the first display member. Depending on the overall geometry and design of the drug delivery device, the first direction may either point in axial direction or along the circumference of an e.g. tubular shaped pen-type injector.

Alternatively, the display arrangement may be designed as an add-on device to be releasably attached to the housing of a drug delivery device. The display arrangement may serve as an indicator to inform the user or patient to conduct a particular action, such as executing a priming procedure or to put a protective cap back onto a distal injection end of the device.

In a further but independent aspect, the invention also relates to a drug delivery device for dispensing of a dose of a medicament. The device comprises a housing and a drive mechanism arranged in said housing. The drive mechanism comprises at least a piston rod to operably engage with a piston of a cartridge. The cartridge is typically to be arranged in the housing or in a housing component, commonly denoted as cartridge holder. The drug delivery device further comprises a display arrangement as described above being visibly arranged in or on the housing.

In preferred embodiments, the display arrangement is adapted to provide at least one of a priming indication, a last stop indication and/or a cap closure indication. It is further of particular benefit, when at least one of first and/or second display members is operably connected with at least one functional ad/or displacable component of the drug delivery device and/or of its drive mechanism. If for instance the first display member is operably coupled with the drive mechanism, indication of a last dose can be automatically provided as soon as the drive mechanism and/or its piston rod reach a characteristic configuration or position after numerous doses have been set and dispensed.

Moreover, it is conceivable that displacement of first and second display members relative to each other is entirely conducted and effectuated by a user himself. For instance, the display arrangement may be used as a reminder device to indicate to a user if a prescribed dose of the medicament has already been taken or whether injection of a next dose is due.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39);

or des Pro36 [Asp28] Exendin-4(1-39), des Pro36 [IsoAsp28] Exendin-4(1-39), des Pro36 [Met(O)14, Asp28] Exendin-4(1-39), des Pro36 [Met(O)14, IsoAsp28] Exendin-4(1-39), des Pro36 [Trp(O2)25, Asp28] Exendin-4(1-39), des Pro36 [Trp(O2)25, IsoAsp28] Exendin-4(1-39), des Pro36 [Met(O)14 Trp(O2)25, Asp28] Exendin-4(1-39), des Pro36 [Met(O)14 Trp(O2)25, IsoAsp28] Exendin-4(1-39), wherein the group-Lys6-NH2 may be bound to the C-terminus of the Exendin-4 derivative;
or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 Exendin-4(1-39)-NH2, H-(Lys)6-des Pro36, Pro37, Pro38 [Trp(O2), Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by $\alpha$, $\delta$, $\epsilon$, $\gamma$, and $\mu$. The type of heavy chain present defines the isotype of antibody; these chains are found in IgA, IgD, IgE, IgG, and IgM antibodies, respectively.

Distinct heavy chains differ in size and composition; $\alpha$ and $\gamma$ contain approximately 450 amino acids and $\delta$ approximately 500 amino acids, while $\mu$ and $\epsilon$ have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains $\gamma$, $\alpha$ and $\delta$ have a constant region composed of three tandem Ig domains, and a hinge region for added flexibility; heavy chains $\mu$ and $\epsilon$ have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by $\lambda$ and $\kappa$. A light chain has two successive domains: one constant domain (CL) and one variable domain (VL). The approximate length of a light chain is 211 to 217 amino acids. Each antibody contains two light chains that are always identical; only one type of light chain, $\kappa$ or $\lambda$, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from its spirit and scope. Further, it is to be noted, that any reference signs used in the appended claims are not to be construed as limiting the scope of the present invention.

BRIEF DESCRIPTION OF THE DRAWINGS

In the following, preferred embodiments of the invention will be described in detail by making reference to the drawings in which.

DETAILED DESCRIPTION

Figure 1:
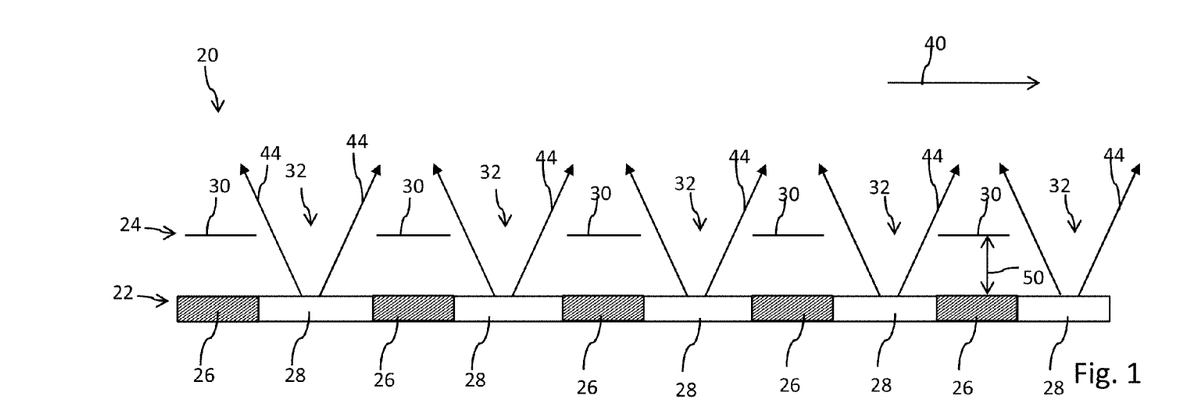
FIG. 1 shows a schematic side view of a display arrangement in a first configuration.

The display arrangement 20 as illustrated in FIG. 1 comprises a first flat and even shaped display member 22 featuring alternately arranged surface portions 26, 28 along a first direction 40. As indicated, all surface portions 26 are interrelated to each other and may be adapted to reveal a first information, which may be a particular color or any kind of symbol, letter or number. In a similar way, also the surface portions 28 separated by surface portions 26 are all interrelated to each other to display a second information that differs from the first information.

For instance, all surface portions 26 may feature a green color and all surface portions 28 may feature a red color. On top of the first display member 22 there is provided a second display member 24 featuring numerous apertures 32 separated by light absorbing cover portions 30. The second display member 24 may comprise a frame-like structure featuring regularly arranged slit-like apertures 32.

The second display member 24 is arranged on top of the first display member 22 in a substantially overlapping manner. Mutual distance 50 between first and second display members 22, 24 may be adapted to alternately reveal or conceal all surface portions 26 or all surface portions 28 of the first display member 22, respectively. First and second display members 22, 24 are overlaid in such a way, that only light 44 emanating from surface portions 28 may propagate through the regularly arranged apertures 32 of the second display member 24 while the light absorbing cover portions 30 of the second display member 24 serve as light absorbing shutters.

Figure 2:
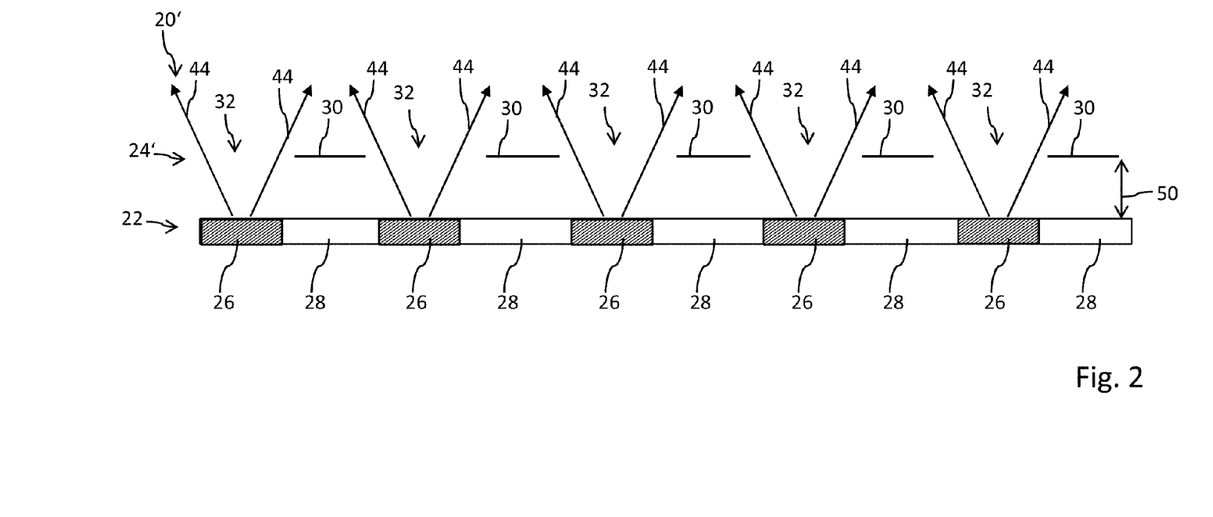
FIG. 2 shows the display element according to FIG. 1 in a second configuration.

The embodiment as illustrated in FIGS. 1 and 2 is designed for reflection geometry. Hence, the second display member 24 also provides a kind of shutter function for the surface portion 26 and therefore substantially impedes that light being incident on the display member 20 hits the surface portions 26.

The periodically arranged surface portions 28 are interrelated to each other in such a way, that all light beams 44 emanating therefrom form or establish a visual information, which may either be a particular and rather unstructured color or which may comprise a symbol, a letter or a number. Accordingly, various surface portions 26 may comprise single fragments of any kind of visually displayable information.

The configuration of the display arrangement 20' according to FIG. 2 differs from the one illustrated in FIG. 1, in that the second display member 24' has been displaced along the direction 40 to the right-hand side in such a way, that light absorbing cover portions 30 of the second display member 24' now substantially overlap with all surface portions 28 of the first display member 22. In this configuration, all surface portions 26 are revealed while surface portions 28 of the first display member 22 are hidden and concealed.

As becomes apparent from FIGS. 1 and 2 mutual displacement of first and second display members 22, 24 may be as small as the extension of a surface portion 26, 28 along the first direction 40. However, the total size of the information complemented by all light beams 44 emanating either form surface portions 26 or 28 exceeds the size of a single surface portion 26, 28 multiple times. Therefore, already by way of a small and hardly visible displacement of first and second display members 22, 24 a rather large, clearly and contrast-enriched visible information complemented by numerous regularly arranged surface portions 26, 28 can be provided.

Figure 3:
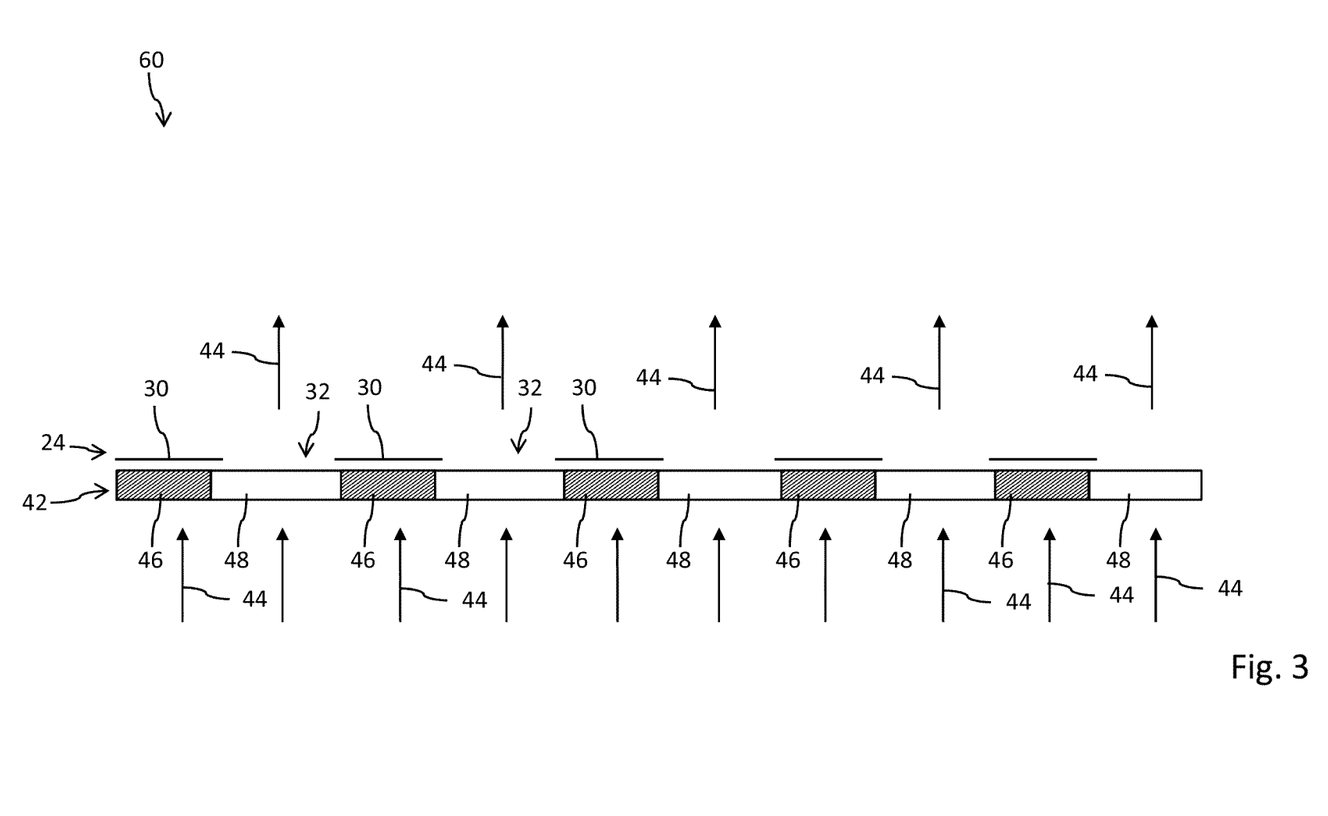
FIG. 3 is illustrative of a display arrangement operating in transmission geometry.

In the embodiment according to FIG. 3, the first display member 22 as shown in FIGS. 1 and 2 has been replaced by a different first display member 42 featuring at least partially transparent alternately arranged surface portions 46, 48. In effect, this modified display arrangement 60 can be operated in transmission geometry, where a light source, not explicitly illustrated, is arranged on the side of the first display member 42 that faces away from the second display member 24.

However, also alternative arrangements of first and second display members 42, 24 are conceivable, wherein the second light modulating display member is arranged between the light source and the first display member carrying readable or visual information.

In an alternative configuration, it is also conceivable, that only selected surface portions 48 are transparent and light transmissive whereas other surface portions 46 are light absorbing and reflective. This way, the different configurations of the display arrangement 60 could be optically enhanced in that surface portions 48 as illustrated in FIG. 3 are actively illuminated by an internal light source whereas in a different configuration, in which the surface portions 46 substantially overlap with the apertures 32 of the second display member 24 substantially absorb the illumination provided from the internal light source and are thus only adapted to provide information in reflection mode.

Figure 4:
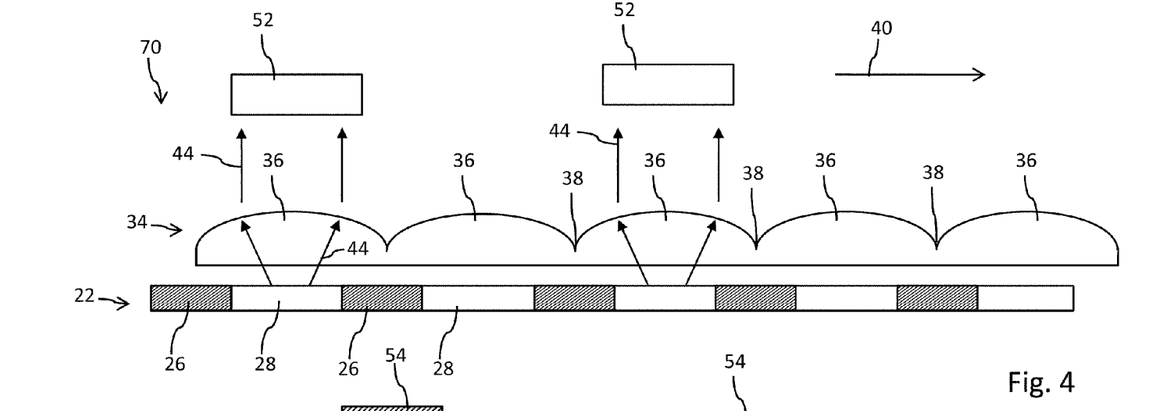
FIG. 4 shows a side view of a display arrangement making use of numerous adjacently disposed lens portions in a first configuration and FIG. 5 shows the display arrangement according to FIG. 4 in a second configuration and FIG. 6 schematically illustrates a pen-type injector equipped with a display arrangement according to the FIGS. 1 to 5.
Figure 5:
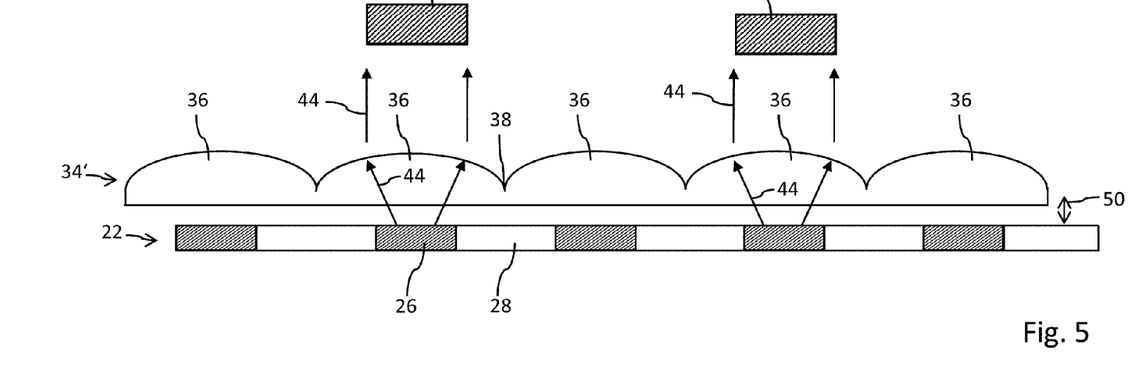

FIGS. 4 and 5 are illustrative of a further embodiment of the display arrangement 70. Here, the second display member 34 comprises numerous magnifying lens portions 36 featuring a periodicity along the first direction 40 that matches with the periodicity of alternately arranged surface portions 26, 28. In the configuration according to FIG. 4, the plane-convex-shaped lens portions 36 of the second display member 34 substantially overlap with the surface portion 28, which will be illustrated to a user in form of a magnified image 52.

The gap portions 38 located between neighbouring or adjacent lens portions 36 substantially overlap with the surface portions 26. Optical rays 44 emanating from the surface portions 26 will be diffracted and/or reflected by the second display member 34 in such a way, that light from those surface portions 26 is almost not visible to a user. This way, surface portions 26 are effectively concealed.

By shifting or displacing first and second display elements 34, 22 relative to each other, e.g. by shifting the second display member 34 to the left as depicted in FIG. 5, light beams 44 emanating from surface portions 26 will be magnified and may result in an enlarge image 54 as shown in FIG. 5. The embodiment according to FIGS. 4 and 5 can be driven both, in reflection and transmission geometry. However, vertical distance 50 and periodicity of surface portions 26, 28 and the geometry of the light modulating structure 36 are typically optimized and interrelate to each other in such a way, that by relative displacement of first and second display members 22, 34 either all surface portions 26 or all surface portions 28 are revealed or concealed, or vice versa.

The embodiment according to FIGS. 4 and 5 is further beneficial in that it provides magnification of the fragmentized information located on and spatially distributed across the various surface portions 26, 28.

Even though, only a one-dimensional relative displacement of first and second display members 22, 24 is illustrated here, the invention can be also generally extended to a two-dimensional displacement of first and second display members, preferably in the plane of their surface portions. Depending on mutual displacement of first and second display members, the first display member may comprise different surface portions arranged e.g. in a chess-board like pattern. Accordingly, the light modulating structure of the second display member may comprise a respective pattern or grating structure.

Figure 6:
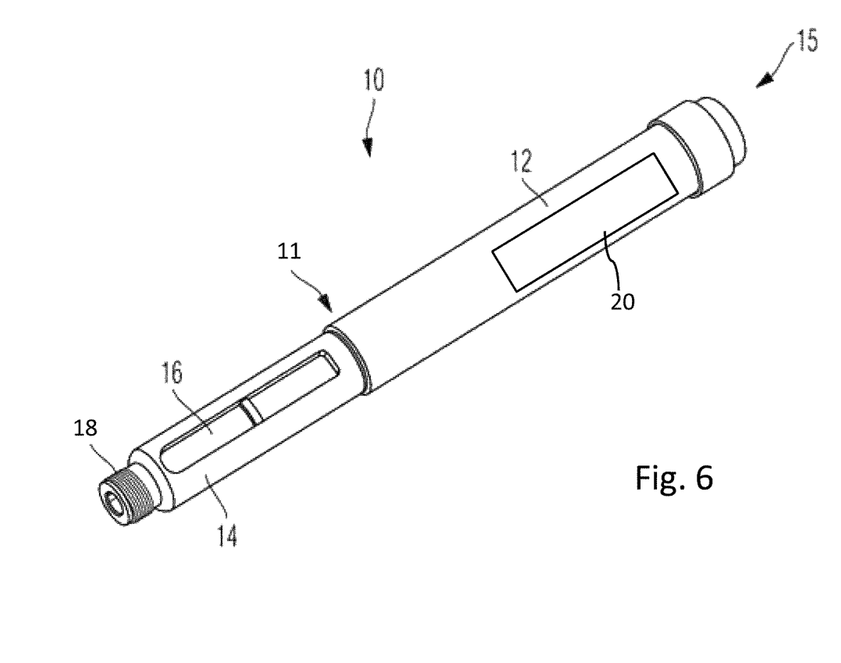

FIG. 6 is further indicative of a drug delivery device 10 of pen-injector type. The device comprises a housing component 12 that serves to accommodate a drive mechanism 11 being not further illustrated here. Distally, that is to the left-hand side in FIG. 6, the drug delivery device 10 comprises a cartridge holder 14 that serves to receive a cartridge 16 filled with a medicament to be dispensed by the device 10. A distal end portion of the cartridge holder 14 comprises a threaded socket 18 in order to threadedly and releasably receive a piercing assembly, by way of which, the medicament contained in the cartridge 16 can be injected into biological tissue.

At an opposite, hence proximal end portion 15, the device 10 comprises a dose dial and/or an injection button, by way of which a user may individually set and/or dispense a dose of the medicament.

As further indicated in FIG. 6, the drug delivery device 10 comprises a display arrangement 20 as illustrated in any one of the preceding FIGS. 1 to 5 in order to visually indicate at least two different configurations of the drug delivery device 10.

Even though only two different surface portions 26, 28 representing different information are described in the various embodiments according to FIGS. 1 to 5, the invention is not limited to illustration of only two different types of information. It is generally conceivable, that numerous, even three, four or even more types of interrelated surface portions are provided on the first display member in order to selectively reveal a respective number of different information.

The invention claimed is:

1. A display arrangement for a drug delivery device, comprising:
 a first display member comprising a plurality of first surface portions and a plurality of second surface portions, wherein the plurality of first surface portions have an interrelated appearance, wherein the plurality of second surface portions have an interrelated appearance, wherein the interrelated appearance of the plurality of first surface portions is different than the interrelated appearance of the plurality of second surface portions, wherein the plurality of first surfaces portions and the plurality of second surface portions are alternately arranged along a first direction, and
 a second display member comprising a light modulating structure to modulate visible light emanating from the first display member,
 wherein the first display member and the second display member are movably disposed relative to each other along the first direction to:
 (i) in a first position, simultaneously reveal the plurality of first surface portions and conceal the plurality of second surface portions, and
 (ii) in a second position, simultaneously conceal the plurality of first surface portions and reveal the plurality of second surface portions.

2. The display arrangement according to claim 1, wherein the first display member and the second display member are arranged at a distance from each other in a substantially overlapping configuration.

3. The display arrangement according to claim 1, wherein at least a portion of the first display member is substantially reflective for light in the visible spectrum.

4. The display arrangement according to claim 1, wherein the plurality of first surface portions of the first display member are periodically arranged along the first direction and the plurality of second surface portions are periodically arranged along the first direction.

5. The display arrangement according to claim 1, wherein the light modulating structure corresponds with the size and with the distance between interrelated surface portions of the first display member.

6. The display arrangement according to claim 4, wherein a periodicity of the plurality of first surface portions of the first display member matches with a periodicity of the light modulating structure of the second display member.

7. The display arrangement according to claim 1, wherein the light modulating structure comprises at least two apertures arranged along the first direction.

8. The display arrangement according to claim 1, wherein the light modulating structure comprises at least two light diffracting portions arranged along the first direction.

9. The display arrangement according to claim 8, wherein the light modulating structure comprises at least two magnifying lens portions adjacently arranged along the first direction.

10. The display arrangement according to claim 1, wherein the plurality of first surface portions of the first display member are interrelated to each other by at least one of the group selected from: a color, a symbol, a number, and a letter.

11. The display arrangement according to claim 1, wherein the light modulating structure comprises at least two light reflecting portions arranged along the first direction.

12. The display arrangement according to claim 1, wherein at least a portion of the first display member is substantially transmissive for light in the visible spectrum.

13. The display arrangement according to claim 12, further comprising:
a housing; and
an internal light source in the housing,
wherein the internal light source is configured to illuminate the plurality of first surface portions, and
wherein the plurality of first surface portions are the at least the portion of the first display member that is substantially transmissive.

14. The display arrangement according to claim 13, wherein the plurality of second surface portions are at least one of light absorbing or reflective.

15. The display arrangement of according to claim 9, wherein each of the at least two magnifying lens portions are separated by a gap portion of the second display member,
wherein, in the first position, each gap portion overlaps a respective one of the plurality of second surface portions,
wherein, in the second position, each gap portion overlaps a respective one of the plurality of first surface portions, and
wherein each gap portion is configured to at least one of diffract light passing from the first display member through the gap portion such that:

(i) in the first position, the plurality of second surface portions are concealed, and
(ii) in the second position, the plurality of first surface portions are concealed.

16. A drug delivery device for dispensing of a dose of a medicament, comprising:
a housing,
a drive mechanism arranged in said housing and comprising a piston rod to operably engage with a piston of a cartridge to be arranged in the housing,
a display arrangement according to claim 1 visibly arranged in or on the housing.

17. The drug delivery device according to claim 16, wherein at least one of the first display member or the second display member is integrated into the housing of the drug delivery device.

18. The drug delivery device according to claim 16, wherein the display arrangement is adapted to provide at least one of a priming indication, a last dose indication, or a cap closure indication.

\* \* \* \* \*